(12) United States Patent
Lee et al.

(10) Patent No.: US 10,813,947 B1
(45) Date of Patent: *Oct. 27, 2020

(54) METHODS OF OTOPROTECTION AGAINST PLATINUM-BASED ANTINEOPLASTIC AGENTS

(71) Applicant: Decibel Therapeutics, Inc., Boston, MA (US)

(72) Inventors: John Lee, Arlington, MA (US); John R. Soglia, Sherborn, MA (US); Qi-Ying Hu, Needham, MA (US); Fuxin Shi, Winchester, MA (US)

(73) Assignee: Decibel Therapeutics, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/427,567

(22) Filed: May 31, 2019

(51) Int. Cl.
- *A61K 33/04* (2006.01)
- *A61K 9/00* (2006.01)
- *A61P 27/16* (2006.01)
- *A61K 47/36* (2006.01)
- *A61K 33/243* (2019.01)

(52) U.S. Cl.
CPC ............ *A61K 33/04* (2013.01); *A61K 9/0004* (2013.01); *A61K 9/0046* (2013.01); *A61P 27/16* (2018.01); *A61K 33/243* (2019.01); *A61K 47/36* (2013.01)

(58) Field of Classification Search
CPC .................................................... A61K 31/10
USPC .......................................................... 424/711
See application file for complete search history.

(56) References Cited

U.S. PATENT DOCUMENTS

| | | |
|---|---|---|
| 6,497,902 B1 | 12/2002 | Ma |
| 6,649,621 B2 | 11/2003 | Kopke et al. |
| 7,790,699 B2 | 9/2010 | Melvik et al. |
| 8,496,957 B2 | 7/2013 | Lichter et al. |
| 8,784,870 B2 | 7/2014 | Lichter et al. |
| 9,427,472 B2 | 8/2016 | Lichter et al. |
| 9,944,524 B2 | 4/2018 | Sherman et al. |
| 10,272,034 B2 | 4/2019 | Lichter et al. |
| 10,596,190 B2 | 3/2020 | Neuwelt |
| 2004/0186172 A1 | 9/2004 | Ibrahim |
| 2013/0045957 A1 | 2/2013 | Piu et al. |
| 2013/0085476 A1 | 4/2013 | Imran |

(Continued)

FOREIGN PATENT DOCUMENTS

| | | |
|---|---|---|
| WO | WO-2017/139684 A1 | 8/2017 |
| WO | WO-2018/136605 A1 | 7/2018 |

(Continued)

OTHER PUBLICATIONS

SIOPEL 6 clinical trials. (NCT00652132 (2015) https://clinicaltrials.gov/ct2/show/NCT00652132 (retrieved from the internet Dec. 11, 2018)). (Year: 2015).*

(Continued)

*Primary Examiner* — Shengjun Wang
(74) *Attorney, Agent, or Firm* — Clark & Elbing LLP

(57) ABSTRACT

Disclosed herein are methods for otoprotection against platinum-based antineoplastic agents by administering a thiosulfate salt to a subject in need thereof. Typically, the thiosulfate salt is administered to the subject scheduled to be administered a platinum-based antineoplastic agent within 4 hours. Alternatively, the thiosulfate salt is administered within 7 hours after the administration of a platinum-based neoplastic agent.

7 Claims, 5 Drawing Sheets

(56) References Cited

U.S. PATENT DOCUMENTS

| | | |
|---|---|---|
| 2017/0182089 A1 | 6/2017 | Neuwelt et al. |
| 2018/0000950 A1 | 1/2018 | Savel et al. |
| 2018/0161297 A1 | 6/2018 | Kirnon et al. |
| 2018/0228903 A1 | 8/2018 | Kohane et al. |
| 2018/0360874 A1 | 12/2018 | Nivoliez |
| 2019/0144276 A1 | 5/2019 | Sherman et al. |
| 2019/0160094 A1 | 5/2019 | Neuwelt |
| 2019/0192425 A1 | 6/2019 | Lichter et al. |
| 2019/0210107 A1 | 7/2019 | Palmer |
| 2019/0336524 A1* | 11/2019 | Hu .................. A61K 9/0019 |
| 2020/0009255 A1 | 1/2020 | Lovelace et al. |
| 2020/0023003 A1 | 1/2020 | Lee et al. |
| 2020/0038436 A1 | 2/2020 | Neuwelt |

FOREIGN PATENT DOCUMENTS

| | | |
|---|---|---|
| WO | WO-2019/108592 A2 | 6/2019 |
| WO | WO-2019/118330 A1 | 6/2019 |
| WO | WO-2019/126783 A1 | 6/2019 |
| WO | WO-2019/140012 A1 | 7/2019 |
| WO | WO-2019/154895 A1 | 8/2019 |
| WO | WO-2019/157370 A1 | 8/2019 |
| WO | WO-2019/210107 A1 | 10/2019 |
| WO | WO-2019/244121 A1 | 12/2019 |

OTHER PUBLICATIONS

Meyer et al. ("Randomized controlled trial to test the efficacy of transtympanic injection of a sodium thiosulfate gel to prevent cisplatin-induced ototoxicity." J. Clinical Oncology, 2017, vol. 35, No. 15, sup. Supplement 1. Abstract EMBASE DN 617627365). (Year: 2017).*

U.S. Appl. No. 16/517,284, Decibel Therapeutics, Inc.

Andersson et al., "Pharmacokinetics of cisplatin and its monohydrated complex in humans," J Pharm Sci. 85(8):824-7 (1996).

Berglin et al., "Prevention of cisplatin-induced hearing loss by administration of a thiosulfate-containing gel to the middle ear in a guinea pig model," Cancer Chemother Pharmacol. 68(6):1547-56 (2011).

Freyer et al., "Interventions for cisplatin-induced hearing loss in children and adolescents with cancer," Lancet Child Adolesc Health. doi: 10.1016/S2352-4642(19)30115-4 (2019) (7 pages).

Johnsson et al., "Pharmacokinetics and tissue distribution of cisplatin in nude mice: platinum levels and cisplatin-DNA adducts," Cancer Chemother Pharmacol. 37(1-2):23-31 (1995).

Khunmanee et al., "Crosslinking method of hyaluronic-based hydrogel for biomedical applications," J Tissue Eng. 8:1-16 (2017).

Leitao et al., "Quantification of sodium thiosulphate protection on cisplatin-induced toxicities," J Otolaryngol. 32(3):146-50 (2003).

Otto et al., "Effects of cisplatin and thiosulfate upon auditory brainstem responses of guinea pigs," Hear Res. 35(1):79-85 (1988).

Pierre, Pernilla, Thesis: "Cisplatin, a platinum-containing antineoplastic drug: perspectives on analytical chemistry and prevention of ototoxicity," Department of Oncology-Pathology, Karolinska Institutet, 2010.

Pierre et al., "Middle ear administration of a particulate chitosan gel in an in vivo model of cisplatin ototoxicity," Front Cell Neurosci. 13(268): (2019) (13 pages).

Schroeder II et al., "Pharmacokinetics of sodium thiosulfate in guinea pig perilymph following middle ear application," J Otol. 13(2):54-8 (2018).

Togawa et al., "High performance liquid chromatographic determination of bound sulfide and sulfite and thiosulfate at their low levels in human serum by pre-column fluorescence derivatization with monobromobimane," Chem Pharm Bull. 40(11):3000-4 (1992).

Urien et al., "Population pharmacokinetics of total and unbound plasma cisplatin in adult patients," Br J Clin Pharmacol. 57(6):756-63 (2004).

Wang et al., "Local application of sodium thiosulfate prevents cisplatin-induced hearing loss in the guinea pig," Neuropharmacology. 45(3):380-93 (2003).

Pestieau et al., "Impact of carrier solutions on pharmacokinetics of intraperitoneal chemotherapy," Cancer Chemother Pharmacol. 47(3):269-76 (2001) (Abstract Only) (2 pages).

Wu et al., "The chemoprotective agent N-acetylcysteine blocks cisplatin-induced apoptosis through caspase signaling pathway," J Pharmacol Exp Ther 312(2):424-31 (2005).

Choi et al., "Perilymph osmolality modulates cochlear function," available in PMC Mar. 14, 2013, published in final edited form as: Laryngoscope. 118(9):1621-9 (2008) (16 pages).

Rolland et al., "A randomized controlled trial to test the efficacy of trans-tympanic injections of a sodium thiosulfate gel to prevent cisplatin-induced ototoxicity in patients with head and neck cancer," J Otolaryngol Head Neck Surg. 48(1):4 (2019) (9 pages).

Wang, "Tolerability of hypertonic injectables," Int J Pharm. 490(1-2):308-15 (2015).

Naert et al., "Use of the guinea pig in studies on the development and prevention of acquired sensorineural hearing loss, with an emphasis on noise," J Acoust Soc Am. 146(5): 3743-69 (2019) (28 pages).

* cited by examiner

METHODS OF OTOPROTECTION AGAINST PLATINUM-BASED ANTINEOPLASTIC AGENTS

FIELD OF THE INVENTION

The present invention provides methods of otoprotection against platinum-based antineoplastic agents.

BACKGROUND

Platinum-based antineoplastic agents (e.g., cisplatin) are chemotherapeutic agents widely used to treat cancers and tumors. These agents are toxic and are known to induce hearing loss both in human and animal models. Thus, patients undergoing chemotherapy with platinum-based antineoplastic agents can suffer from hearing loss. There is a need for otoprotective compositions and methods to prevent or mitigate hearing loss associated with chemotherapeutic regimens including platinum-based antineoplastic agents.

SUMMARY OF THE INVENTION

In general, the invention provides methods for mitigating platinum-induced ototoxicity in a subject in need thereof. The method involves administering to the subject an effective amount of a thiosulfate salt.

In some embodiments, the subject was administered a platinum-based neoplastic agent not more than 7 hours prior administering the thiosulfate salt or is scheduled to be administered a platinum-based antineoplastic agent within 4 hours. In certain embodiments, the subject was administered a platinum-based neoplastic agent not more than 7 hours prior administering the thiosulfate salt. In particular embodiments, the subject is scheduled to be administered a platinum-based antineoplastic agent within 4.5 hours. In further embodiments, the subject was administered a platinum-based neoplastic agent not more than 2.5 hours prior to administering the thiosulfate salt. In yet further embodiments, the subject was administered a platinum-based neoplastic agent not more than 1 hour prior to administering the thiosulfate salt.

In some embodiments, administration of an effective amount of a thiosulfate salt to the subject produces a plasma thiosulfate $C_{max}$ that is 30 μM or less at the time of administration a platinum-based antineoplastic agent. In certain embodiments, administration of an effective amount of a thiosulfate salt to the subject produces a cochlear thiosulfate $C_{max}$ is at least 30 times greater than a cochlear $C_{max}$ of the platinum-based antineoplastic agent. The cochlear platinum concentrations and the cochlear $C_{max}$ are typically modeled by a pharmacokinetic simulation of intravenous infusion in a two-compartment model. For example, the pharmacokinetic simulation may be conducted using WinNonlin (Phoenix 64) PK simulation model 9 (IV infusion, 2 compartment).

In still further embodiments, the thiosulfate salt is administered auricularly. In certain embodiments, the thiosulfate salt is administered intratympanically, transtympanically, or by inner ear injection. In particular embodiments, the thiosulfate salt is administered transtympanically or by inner ear injection.

In some embodiments, the method further includes administering the platinum-based antineoplastic agent.

In certain embodiments, the thiosulfate salt is an alkaline thiosulfate salt, ammonium thiosulfate salt, or a solvate thereof. In further embodiments, the effective amount of a thiosulfate salt is administered as a hypertonic pharmaceutical composition comprising the effective amount of a thiosulfate salt. In yet further embodiments, 200-1,000 μL (e.g., 200-900 μL, 200-800 μL, 200-700 μL, 200-600 μL, 200-500 μL, 200-400 μL, 200-300 μL, 300-900 μL, 300-800 μL, 300-700 μL, 300-600 μL, 300-500 μL, 300-400 μL, 400-900 μL, 400-800 μL, 400-700 μL, 400-600 μL, or 400-500 μL) of the hypertonic pharmaceutical composition are administered to the round window of the subject.

In still further embodiments, the calculated osmolarity of the hypertonic pharmaceutical composition is 500-5,000 mOsm/L (e.g., 600-5,000 mOsm/L, 700-5,000 mOsm/L, 800-5,000 mOsm/L, 900-5,000 mOsm/L, 1,000-5,000 mOsm/L, 1,500-5,000 mOsm/L, 2,000-5,000 mOsm/L, 2,500-5,000 mOsm/L, 3,000-5,000 mOsm/L, 500-4,000 mOsm/L, 600-4,000 mOsm/L, 700-4,000 mOsm/L, 800-4,000 mOsm/L, 900-4,000 mOsm/L, 1,000-4,000 mOsm/L, 1,500-4,000 mOsm/L, 2,000-4,000 mOsm/L, 2,500-4,000 mOsm/L, 3,000-4,000 mOsm/L, 500-3,000 mOsm/L, 600-3,000 mOsm/L, 700-3,000 mOsm/L, 800-3,000 mOsm/L, 900-3,000 mOsm/L, 1,000-3,000 mOsm/L, 1,500-3,000 mOsm/L, 2,000-3,000 mOsm/L, 2,500-3,000 mOsm/L, 500-2,500 mOsm/L, 600-2,500 mOsm/L, 700-2,500 mOsm/L, 800-2,500 mOsm/L, 900-2,500 mOsm/L, 1,000-2,500 mOsm/L, 1,500-2,500 mOsm/L, 2,000-2,500 mOsm/L, 500-2,000 mOsm/L, 600-2,000 mOsm/L, 700-2,000 mOsm/L, 800-2,000 mOsm/L, 900-2,000 mOsm/L, 1,000-2,000 mOsm/L, 1,500-2,000 mOsm/L, 500-1,500 mOsm/L, 600-1,500 mOsm/L, 700-1,500 mOsm/L, 800-1,500 mOsm/L, 900-1,500 mOsm/L, or 1,000-1,500 mOsm/L).

In some embodiments, the concentration of the thiosulfate salt in the hypertonic pharmaceutical composition is 0.5M-2.5M (e.g., about 0.05M to about 1.5 M, about 0.05M to about 0.5M, about 0.05M to about 0.2M, about 0.05M to about 0.1 M, about 0.1 M to about 1.5M, about 0.1 M to about 0.5M, about 0.1 M to about 0.2M, about 0.2M to about 1.5M, about 0.2M to about 0.5M, about 0.5M to about 1.5M, 0.05M to about 1.0 M, about 0.05M to about 0.5M, about 0.05M to about 0.2M, about 0.05M to about 0.1 M, about 0.1 M to about 1.0M, about 0.1 M to about 0.5M, about 0.1 M to about 0.2M, about 0.2M to about 1.0M, about 0.2M to about 0.5M, about 0.5M to about 1.0M, or about 1.0M to about 1.5M).

In certain embodiments, the effective amount is an amount that produces a plasma thiosulfate concentration that is 30 μM or less at the time the platinum-based antineoplastic agent is administered. In certain embodiments, the effective amount is 0.1-2.5 mmol of the thiosulfate salt. In particular embodiments, the effective amount is an amount that produces a maximum thiosulfate concentration of 0.6-10 mmol/L by 1 h post administration. In further embodiments, the effective amount is an amount that produces a thiosulfate concentration of 0.1-2 mmol/L by 7 h post administration in the subject's cochlea.

In yet further embodiments, the invention is described by the following enumerated items.

1. A method of mitigating platinum-induced ototoxicity in a subject in need thereof, the method comprising administering to the subject an effective amount of a thiosulfate salt, wherein the subject was administered a platinum-based neoplastic agent not more than 7 hours prior administering the thiosulfate salt or is scheduled to be administered a platinum-based antineoplastic agent within 4 hours.

2. The method of item 1, wherein the effective amount is an amount that produces a plasma thiosulfate concentration that is 30 μM or less at the time the platinum-based antineoplastic agent is administered.

3. A method of mitigating platinum-induced ototoxicity in a subject in need thereof, the method comprising administering to the subject an effective amount of a thiosulfate salt to produce (i) a plasma thiosulfate $C_{max}$ that is 30 μM or less at the time of administration a platinum-based antineoplastic agent and (ii) a cochlear thiosulfate $C_{max}$ is at least 30 times greater than a cochlear $C_{max}$ of the platinum-based antineoplastic agent, wherein the cochlear platinum concentrations and the cochlear $C_{max}$ are modeled by a pharmacokinetic simulation of intravenous infusion in a two compartment model.

4. The method of item 2, wherein the subject was administered a platinum-based neoplastic agent not more than 7 hours prior administering the thiosulfate salt or is scheduled to be administered a platinum-based antineoplastic agent within 4 hours 5. The method of any one of items 1 to 3, wherein the subject was administered a platinum-based neoplastic agent not more than 7 hours prior administering the thiosulfate salt.

6. The method of any one of items 1 to 3, wherein the subject was administered a platinum-based neoplastic agent not more than 6 hours prior administering the thiosulfate salt.

7. The method of any one of items 1 to 3, wherein the subject was administered a platinum-based neoplastic agent not more than 5 hours prior administering the thiosulfate salt.

8. The method of any one of items 1 to 3, wherein the subject was administered a platinum-based neoplastic agent not more than 4 hours prior administering the thiosulfate salt.

9. The method of any one of items 1 to 3, wherein the subject was administered a platinum-based neoplastic agent not more than 3 hours prior administering the thiosulfate salt.

10. The method of any one of items 1 to 3, wherein the subject was administered a platinum-based neoplastic agent not more than 2.5 hours prior to administering the thiosulfate salt.

11. The method of any one of items 1 to 3, wherein the subject was administered a platinum-based neoplastic agent not more than 2 hours prior administering the thiosulfate salt.

12. The method of any one of items 1 to 3, wherein the subject was administered a platinum-based neoplastic agent not more than 1 hour prior administering the thiosulfate salt.

13. The method of any one of items 1 to 3, wherein the subject is scheduled to be administered a platinum-based antineoplastic agent within 4.5 hours.

14. The method of any one of items 1 to 3, wherein the subject is scheduled to be administered a platinum-based antineoplastic agent within 4 hours.

15. The method of any one of items 1 to 3, wherein the subject is scheduled to be administered a platinum-based antineoplastic agent within 3 hours.

16. The method of any one of items 1 to 3, wherein the subject is scheduled to be administered a platinum-based antineoplastic agent within 2 hours.

17. The method of any one of items 1 to 3, wherein the subject is scheduled to be administered a platinum-based antineoplastic agent within 1 hour.

18. The method of any one of items 1 to 16, wherein the thiosulfate salt is administered auricularly.

19. The method of item 17, wherein the thiosulfate salt is administered intratympanically.

20. The method of item 17, wherein the thiosulfate salt is administered transtympanically.

21. The method of item 17, wherein the thiosulfate salt is administered by inner ear injection.

22. The method of any one of items 1 to 20, further comprising administering the platinum-based antineoplastic agent.

23. The method of any one of items 1 to 21, wherein the thiosulfate salt is an alkaline thiosulfate salt, ammonium thiosulfate salt, or a solvate thereof.

24. The method of any one of items 1 to 22, wherein the effective amount of a thiosulfate salt is administered as a hypertonic pharmaceutical composition comprising the effective amount of a thiosulfate salt.

25. The method of item 23, wherein 200-1,000 μL of the hypertonic pharmaceutical composition are administered to the round window of the subject.

26. The method of item 23 or 24, wherein the calculated osmolarity of the hypertonic pharmaceutical composition is 500-5,000 mOsm/L.

27. The method of any one of items 23 to 25, wherein the concentration of the thiosulfate salt in the hypertonic pharmaceutical composition is 0.5M-2.5M.

28. The method of any one of items 23 to 25, wherein the concentration of the thiosulfate salt in the hypertonic pharmaceutical composition is 0.5M-1.5M.

29. The method of any one of items 23 to 25, wherein the concentration of the thiosulfate salt in the hypertonic pharmaceutical composition is 0.5M-1.0M.

30. The method of any one of items 1 to 28, wherein the effective amount is at least 0.05 mmol of the thiosulfate salt.

31. The method of any one of items 1 to 28, wherein the effective amount is at least 0.1 mmol of the thiosulfate salt.

32. The method of any one of items 1 to 28, wherein the effective amount is at least 0.2 mmol of the thiosulfate salt.

33. The method of any one of items 1 to 28, wherein the effective amount is at least 0.3 mmol of the thiosulfate salt.

34. The method of any one of items 1 to 28, wherein the effective amount is at least 0.4 mmol of the thiosulfate salt.

35. The method of any one of items 1 to 33, wherein the effective amount is 2.5 mmol or less of the thiosulfate salt.

36. The method of any one of items 1 to 33, wherein the effective amount is 2.0 mmol or less of the thiosulfate salt.

37. The method of any one of items 1 to 33, wherein the effective amount is 1.5 mmol or less of the thiosulfate salt.

38. The method of any one of items 1 to 33, wherein the effective amount is 1.0 mmol or less of the thiosulfate salt.

39. The method of any one of items 1 to 33, wherein the effective amount is 0.5 mmol or less of the thiosulfate salt.

40. The method of any one of items 1 to 38, wherein the effective amount is an amount that produces a maximum thiosulfate concentration of 0.6-10 mmol/L by 1 h post administration.

41. The method of any one of items 1 to 39, wherein the effective amount is an amount that produces a thiosulfate concentration of 0.1-2 mmol/L by 7 h post administration in the subject's cochlea.

Definitions

The term "about," as used herein, represents a value that is in the range of ±10% of the value that follows the term "about."

The term "alkaline salt," as used herein, represents a sodium or potassium salt of a compound. Alkaline salts may be monobasic or, if the number of acidic moieties (e.g., —COOH, —SO$_3$H, or —P(O)(OH)$_n$ moieties) permits, dibasic or tribasic.

The term "ammonium salt," as used herein, represents an NH$_4$+ salt of a compound. Ammonium salts may be monobasic or, if the number of acidic moieties (e.g., —COOH, —SO$_3$H, or —P(O)(OH)$_n$ moieties) permits, dibasic or tribasic.

The term "gelling agent," as used herein, refers to pharmaceutically acceptable excipient known in the art to produce a gel upon mixing with a solvent (e.g., an aqueous solvent). Non-limiting examples of gelling agents include hyaluronan, a polyoxyethylene-polyoxypropylene block copolymer (e.g., a poloxamer), poly(lactic-co-glycolic) acid, polylactic acid, polycaprolactone, alginic acid or a salt thereof, polyethylene glycol, a cellulose, a cellulose ether, a carbomer (e.g., Carbopol®), agar-agar, gelatin, glucomannan, galactomannan (e.g., guar gum, locust bean gum, or tara gum), xanthan gum, chitosan, pectin, starch, tragacanth, carrageenan, polyvinylpyrrolidone, polyvinyl alcohol, paraffin, petrolatum, silicates, fibroin, and combinations thereof.

The term "hypertonic," as used herein in reference to pharmaceutical compositions, represents a pharmaceutical composition having a calculated osmolarity of 300 mOsm/L to 7,000 mOsm/L (e.g., 300 mOsm/L to 2,500 mOsm/L), which corresponds to 300 mmol to 7,000 mmol (e.g., 300 mOsm/L to 2,500 mmol) of ions and/or neutral molecules produced by dissolution of platinum-deactivating agent and any ionic, non-polymeric excipients in 1 L of solvent having calculated osmolarity of 0 mOsm/L. For the purpose of the present disclosure, the calculated osmolarity does not include ions and/or neutral molecules produced from polymeric excipients (e.g., from a gelling agent). For the purpose of this disclosure, polymeric excipients (e.g., a gelling agents) are deemed as not contributing to the calculated osmolarity of the compositions disclosed herein.

The term "intratympanic," as used herein in reference to a route of administration, means delivery to the round window by injection or infusion through an ear canal with a temporarily removed or lifted tympanic membrane or through a port created through an auditory bulla into the middle ear of a subject.

The term "pharmaceutical composition," as used herein, represents a composition formulated with a pharmaceutically acceptable excipient, and manufactured or sold with the approval of a governmental regulatory agency as part of a therapeutic regimen for the treatment of disease in a mammal.

The term "pharmaceutical dosage form," as used herein, represents those pharmaceutical compositions intended for administration to a subject as is without further modification (e.g., without dilution with, suspension in, or dissolution in a liquid solvent).

The term "pharmaceutically acceptable excipient," as used herein, refers to any ingredient other than the thiosulfate salts and gelling agents described herein (e.g., a vehicle capable of suspending or dissolving the active compound) and having the properties of being substantially non-toxic and substantially non-inflammatory in a patient. Excipients may include, e.g., antioxidants, disintegrants, dyes (colors), emollients, emulsifiers, fillers (diluents), flavors, fragrances, preservatives, printing inks, sorbents, suspending or dispersing agents, sweeteners, liquid solvents, and buffering agents.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "pharmaceutically acceptable solvate" as used herein means a compound as described herein wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, tri-, tetra-, and pentahydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When the solvate is water-based, the solvate is referred to as a hydrate.

The term "platinum-based antineoplastic agent," as used herein, represents a coordination compound of Pt(II) or Pt(IV). Platinum-based antineoplastic agents are known in the art as platins. Typically, platinum-based antineoplastic agents include at least two coordination sites at the platinum center that are occupied by nitrogenous spectator ligand(s). The nitrogenous spectator ligands are monodentate or bidentate ligands, in which the donor atom is an sp$^3$- or sp$^2$- hybridized nitrogen atom within the ligand. Non-limiting examples of nitrogenous spectator ligands are ammonia, 1,2-cyclohexanediamine, a picoline, phenanthrin, or 1,6-hexanediamine. Non-limiting examples of platinum-based antineoplastic agents include cisplatin, carboplatin, oxaliplatin, nedaplatin, triplatin tetranitrate, phenanthriplatin, picoplatin, and satraplatin.

The term "subject," as used herein, refers to an animal (e.g., a mammal, e.g., a human). A subject to be treated according to the methods described herein may be one who is being treated with a therapeutic regimen including a platinum-based antineoplastic agent (e.g., for the treatment of a benign tumor, malignant tumor, or cancer). The subject may have been diagnosed with a benign tumor, malignant tumor, or cancer by any method or technique known in the art. One skilled in the art will understand that a subject to be treated according to the invention may have been subjected to standard tests or may have been identified, without examination, as one at high risk due to receiving a therapeutic regimen including a platinum-based antineoplastic agent.

The term "substantially neutral," used herein, refers to a pH level of 5.5 to about 8.5, as measured at 20° C.

The term "tonicity agent," as used herein, refers to a class of pharmaceutically acceptable excipients that are used to control osmolarity of pharmaceutical compositions. Non-limiting examples of a tonicity agent include substantially neutral buffering agents (e.g., phosphate buffered saline, tris buffer, or artificial perilymph), dextrose, mannitol, glycerin, potassium chloride, and sodium chloride (e.g., as a hypertonic, isotonic, or hypotonic saline). Artificial perilymph is an aqueous solution containing NaCl (120-130 mM), KCl (3.5 mM), $CaCl_2$ (1.3-1.5 mM), $MgCl_2$ (1.2 mM), glucose (5.0-11 mM), and buffering agents (e.g., $NaHCO_3$ (25 mM) and $NaH_2PO_4$ (0.75 mM), or HEPES (20 mM) and NaOH (adjusted to pH of about 7.5)).

The term "transtympanic," as used herein, in reference to a route of administration, means delivery to the round window by injection or infusion across tympanic membrane. A transtympanic injection may be performed directly through the tympanic membrane or through a tube embedded in the tympanic membrane (e.g., through a tympanostomy tube or grommet).

The term "inner ear injection," as used herein, refers to the direct injection of drug into the inner ear space.

DETAILED DESCRIPTION

Figure 1:
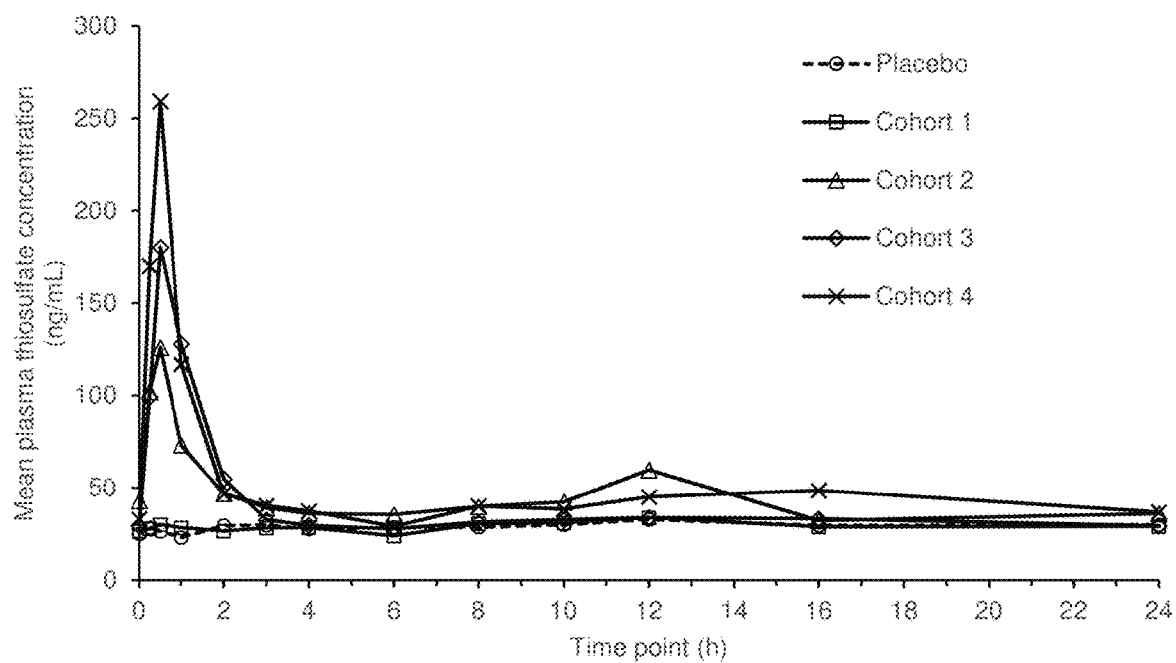
FIG. 1 is a chart showing the profiles (0-24 h) of mean plasma thiosulfate concentrations over time for each tested human cohort. The X-axis shows time (h), and the Y-axis shows mean plasma thiosulfate concentrations (ng/mL).

In general, the invention provides method of mitigating platinum-induced ototoxicity in a subject by administering to the subject an effective amount of a thiosulfate salt. Preferably, the thiosulfate salt is administered auricularly (e.g., intratympanically or transtympanically).

Typically, the thiosulfate salt is administered to the subject scheduled to be administered a platinum-based antineoplastic agent within 4 hours (e.g., within 3 hours, within 2 hours, or within 1 hour). Alternatively, the thiosulfate salt is administered within 7 hours (e.g., within 6 hours, within 5 hours, within 4 hours, within 3 hours, within 2 hours, or within 1 hour) after the administration of a platinum-based neoplastic agent. Preferably, the thiosulfate salt is administered to the subject scheduled to be administered platinum-based antineoplastic agent within 3 hours. Alternatively, the thiosulfate salt is administered within 4 hours after the administration of a platinum-based neoplastic agent. More preferably, the thiosulfate salt is administered to the subject scheduled to be administered platinum-based antineoplastic agent within 1 hour. Alternatively, the thiosulfate salt is administered within 1 hour after the administration of a platinum-based neoplastic agent.

An effective amount of a thiosulfate salt typically produces a plasma thiosulfate concentration that is 30 µM or less (e.g., 20 µM or less, 10 µM or less, or near endogenous concentration) at the time of administration a platinum-based antineoplastic agent. Additionally or alternatively, an effective amount of a thiosulfate salt typically produces a cochlear thiosulfate concentration that is at least 30 times greater (e.g., 30 to 1000 times greater, 30 to 500 times greater, or 30 to 150 times greater) than a cochlear $C_{max}$ of the platinum-based antineoplastic agent, wherein the cochlear platinum concentrations and the cochlear $C_{max}$ are modeled by a pharmacokinetic simulation of intravenous infusion in a two compartment model.

Platinum-induced ototoxicity may occur in subjects receiving a platinum-based antineoplastic agent (e.g., a subject having a tumor or cancer). Non-limiting examples of the platinum-based antineoplastic agents include cisplatin, carboplatin, oxaliplatin, nedaplatin, triplatin tetranitrate, phenanthriplatin, picoplatin, and satraplatin.

A thiosulfate salt may mitigate (e.g., eliminate) hearing loss in a subject receiving a platinum-based antineoplastic agent, as measured by at least 50% (e.g., at least 60%, at least 70%, or at least 80%) reduction in the sound pressure level threshold elevation in the subject at a frequency 8 kHz or higher (e.g., between 8 kHz and 20 kHz) relative to a reference subject that receives the same platinum-based antineoplastic agent regimen but does not receive the thiosulfate salt.

Thiosulfate salts may exhibit otoprotective properties against platinum-based antineoplastic agents and may be used in a method of mitigating (e.g., eliminating) platinum-induced ototoxicity in subjects in need thereof. Typically, a thiosulfate salt is administered to a round window of the subject. The subject may be undergoing therapy with a platinum-based antineoplastic agent (e.g., cisplatin, carboplatin, oxaliplatin, nedaplatin, triplatin tetranitrate, phenanthriplatin, picoplatin, or satraplatin).

A thiosulfate salt may be administered to a subject, e.g., before or after the administration of a platinum-based antineoplastic agent to the subject. Alternatively, a thiosulfate salt may be administered, e.g., at the same time as the administration of a platinum-based antineoplastic agent. A thiosulfate salt may be administered to a subject scheduled to be administered a platinum-based antineoplastic agent within 4 hours, e.g., within 3 hour, within 2 hours, or within 1 hour (e.g., at least 5 minute, at least 15 minutes, or at least 30 minutes prior to platinum-based antineoplastic agent administration). Alternatively, a thiosulfate salt may be administered, e.g., not more than 7 hours (e.g., not more than 6 hours, not more than 5 hours, not more than 4 hours, not more than 3 hours, not more than 2 hours, or not more than 1 hour) after platinum-based antineoplastic agent administration (e.g., at least 5 minutes, at least 15 minutes, or at least 30 minutes after).

Typically, the pharmaceutical composition of the invention may be administered by a route different from the platinum-based antineoplastic agent. The methods of the invention may utilize a local route of administration, for example, the pharmaceutical composition of the invention may be administered intratympanically or transtympanically. Transtympanic administration may include injection or infusion of an effective amount of the pharmaceutical composition of the invention through the tympanic membrane into the tympanic cavity, thereby providing the anti-platinum chemoprotectant agent to the round window.

In the methods of the invention, typically, a needle is used to pierce the tympanic membrane to instill drug into the middle ear space or traverse an existing PE tube or perforation of the ear drum to instill drug. A separate ventilation hole in the tympanic membrane may or may not be created to allow air to escape the middle ear space. The instilled drug may then target middle ear structures, cells or be designed to enter the inner ear via the round and oval membranes to affect specific targets. This may be accomplished, e.g., by instilling drug through the round window membrane, the oval window, a cochleostomy, or labrinthotomy approach. These surgical procedures may be accomplished by raising a tympanomeatal flap (lifting up the ear drum) and exposing the round window, stapes/oval window and promontory. A stapedotomy hole may be created in the footplate and the drug instilled into the vestibule by pump, injection, or some other method. Alternatively, the bony lip of the round window (RW) is removed (typically by drill) to expose the RW. The RW may then be pierced with a needle and the drug infused or the RW may be fenestrated and the drug instilled directly through the fenestration. Finally, an entirely separate entrance hole to the cochlea may be opened by drilling a cochleostomy hole into the cochlea and drug instilled.

Alternatively, rather than raising a tympanomeatal flap, a mastoidectomy may be performed and the facial recess opened to provide direct access to the oval and round windows as well as the promontory and the semicircular canals. Via this approach, all three sites can be used as just described. In addition, the labyrinth may be opened, much like a cochleostomy, for the instillation of drug. To dissipate fluid/pressure buildup in the inner ear, a separate opening into the RW or OW may be created to allow for excess perilymph to leak out.

Thiosulfate salts may be provided in a pharmaceutical composition. Pharmaceutical compositions may be, e.g., hypertonic. Without wishing to be bound by theory, the higher tonicity of the pharmaceutical compositions disclosed herein is believed to improve the bioavailability of thiosulfate at the round window of a subject, relative to compositions with lower tonicity (e.g., hypotonic or isotonic). The bioavailability is typically calculated using exposure (AUC) to thiosulfate following its administration to a subject. The calculated osmolarity of the pharmaceutical composition (e.g., pharmaceutical dosage form) may be, e.g., at least 400 mOsm/L (e.g., at least 500 mOsm/L, at least 600 mOsm/L, at least 700 mOsm/L, at least 800 mOsm/L, at least 900 mOsm/L, at least 1,000 mOsm/L, at least 1,500 mOsm/L, at least 2,000 mOsm/L, at least 2,500 mOsm/L, or at least 3,000 mOsm/L), and/or 5,000 mOsm/L or less (e.g., 4,000 mOsm/L or less, 3,000 mOsm/L or less, 2,000 mOsm/L or less, 1,900 mOsm/L or less, 1,800 mOsm/L or less, 1,700 mOsm/L or less, 1,600 mOsm/L or less, or 1,500 mOsm/L or less). The calculated osmolarity of the pharmaceutical composition (e.g., pharmaceutical dosage form) may be, e.g., 1,500-4,500 mOsm/L. The calculated osmolarity of the pharmaceutical composition (e.g., pharmaceutical dosage forms) may be, e.g., 3,000-4,500 mOsm/L. The measured osmolality of the pharmaceutical composition (e.g., pharmaceutical dosage form) may be, e.g., at least 0.3 Osm/kg (e.g., at least 0.5 Osm/kg, at least 0.6 Osm/kg, at least 0.7 Osm/kg, at least 0.8 Osm/kg, at least 0.9 Osm/kg, at least 1.0 Osm/kg, at least 1.2 Osm/kg, at least 1.4 Osm/kg, or at least 1.8 Osm/kg). The measured osmolality of the pharmaceutical composition (e.g., pharmaceutical dosage form) may be, e.g., 2.5 Osm/kg or less (e.g., 2.1 Osm/kg or less). The measured osmolality of the pharmaceutical composition (e.g., pharmaceutical dosage form) may be, e.g., 0.3-2.5 Osm/kg (e.g., 0.5-2.5 Osm/kg, 0.6-2.5 Osm/kg, 0.7-2.5 Osm/kg, 0.8-2.5 Osm/kg, 0.9-2.5 Osm/kg, 1.0-2.5 Osm/kg, 1.2-2.5 Osm/kg, 1.4-2.5 Osm/kg, 1.8-2.5 Osm/kg, 0.5-2.1 Osm/kg, 0.6-2.1 Osm/kg, 0.7-2.1 Osm/kg, 0.8-2.1 Osm/kg, 0.9-2.1 Osm/kg, 1.0-2.1 Osm/kg, 1.2-2.1 Osm/kg, 1.4-2.1 Osm/kg, or 1.8-2.1 Osm/kg). "Calculated osmolarity" refers to the number of mmoles of ions and/or neutral molecules produced by dissolution of one or more compounds in 1 L of DI or distilled water; calculated osmolarity does not include ions and/or neutral molecules produced from polymeric excipients (e.g., from a gelling agent). "Measured osmolality" refers to the osmolality of a composition, as measured using an osmometer (typically, a membrane osmometer).

A preferred pharmaceutical dosage form of the invention is a gel.

In some embodiments, at least 50 µL (preferably, at least 100 µL; more preferably, at least 200 µL) of the pharmaceutical composition are administered to the round window of the subject. In particular embodiments, 1 mL or less (e.g., 0.8 mL or less or 0.5 mL or less) of the pharmaceutical composition are administered to the round window of the subject. In certain embodiments, 100 µL to 1 mL (e.g., 200 µL to 1 mL, 100 µL to 0.8 mL, 200 µL to 0.8 mL, 100 µL to 0.5 mL, 200 µL to 0.5 mL, 0.5 mL to 1.0 mL, 0.5 mL to 0.8 mL, or 0.8 mL to 1.0 mL) of the pharmaceutical composition are administered to the round window of the subject.

A thiosulfate salt may be, e.g., the sole compound contributing to osmolarity of a pharmaceutical composition. Alternatively, higher osmolalities than those afforded by the desired concentration of a thiosulfate salt may be achieved, e.g., through the use of tonicity agents. A tonicity agent may be present in a hypertonic, isotonic, or hypotonic excipient (e.g., a hypotonic liquid solvent). Non-limiting examples of tonicity agents include substantially neutral buffering agents (e.g., phosphate buffered saline, tris buffer, or artificial perilymph), dextrose, mannitol, glycerin, glycerol, potassium chloride, and sodium chloride (e.g., as a hypertonic, isotonic, or hypotonic saline).

Thiosulfate Salts

Without wishing to be bound by theory, thiosulfate salts are believed to reduce or eliminate the toxicity of platinum-based antineoplastic agents by competitively ligating and substantially coordinatively saturating the platinum centers present in the platinum-based antineoplastic agents. The concentration of a thiosulfate salt in a pharmaceutical composition (e.g., a pharmaceutical dosage form) may be, e.g., at least about 0.05M (e.g., at least about 0.1 M, at least about 0.2M, at least about 0.3M, at least about 0.4M, at least about 0.5M, or at least about 1 M). The concentration of a thiosulfate salt in a pharmaceutical composition (e.g., a pharmaceutical dosage form) may be, e.g., about 2.5M or less (e.g., 2.0M or less, 1.5M or less, 1.0M or less, 0.5M or less, about 0.3M or less, or about 0.2M or less). Non-limiting examples of the concentrations of a thiosulfate salt in a pharmaceutical composition (e.g., a pharmaceutical dosage form) may be, e.g., about 0.05M to about 1.5 M, about 0.05M to about 0.5M, about 0.05M to about 0.2M, about 0.05M to about 0.1 M, about 0.1 M to about 1.5M, about 0.1 M to about 0.5M, about 0.1 M to about 0.2M, about 0.2M to about 1.5M, about 0.2M to about 0.5M, about 0.5M to about 1.5M, 0.05M to about 1.0 M, about 0.05M to about 0.5M, about 0.05M to about 0.2M, about 0.05M to about 0.1 M, about 0.1 M to about 1.0M, about 0.1 M to about 0.5M, about 0.1 M to about 0.2M, about 0.2M to about 1.0M, about 0.2M to about 0.5M, or about 0.5M to about 1.0M, or about 1.0M to about 1.5M. Preferably, the concentration of a thiosulfate salt agent in a pharmaceutical composition (e.g., a pharmaceutical dosage form) is about 0.5M to about 1.5M. More preferably, the concentration of a thiosulfate salt agent in a pharmaceutical composition (e.g., a pharmaceutical dosage form) is about 0.5M to about 1.0M.

Preferably, the thiosulfate salt is an alkaline or ammonium thiosulfate salt. More preferably, the thiosulfate salt is sodium thiosulfate.

Gelling Agents

Pharmaceutical compositions disclosed herein include a gelling agent. Gelling agents may be used to increase the viscosity of the pharmaceutical composition, thereby improving the retention of the pharmaceutical composition at the targeted site. Pharmaceutical compositions (e.g., pharmaceutical dosage forms) may contain, e.g., about 0.1% to about 25% (w/v) (e.g., about 0.1% to about 20% (w/v), about 0.1% to about 10% (w/v), about 0.1% to about 2% (w/v), about 0.5% to about 25% (w/v), about 0.5% to about 20% (w/v), about 0.5% to about 10% (w/v), about 0.5% to about 2% (w/v), about 1% to about 20% (w/v), about 1% to about 10% (w/v), about 1% to about 2% (w/v), about 5% to about 20% (w/v), about 5% to about 10% (w/v), or about 7% to about 10% (w/v)) of a gelling agent relative to solvent. Preferably, pharmaceutical compositions (e.g., pharmaceutical dosage forms) may contain, e.g., about 0.5% to about 25% (w/v) (e.g., about 0.5% to about 20% (w/v), about 0.5% to about 10% (w/v), about 0.5% to about 2% (w/v), about 1% to about 20% (w/v), about 1% to about 10% (w/v), about 1% to about 2% (w/v), about 5% to about 20% (w/v), about 5% to about 10% (w/v), or about 7% to about 10% (w/v)) of a gelling agent relative to solvent.

Gelling agents that may be used in the pharmaceutical compositions disclosed herein are known in the art. Non-limiting examples of gelling agents include hyaluronan, a polyoxyethylene-polyoxypropylene block copolymer (e.g., a poloxamer), poly(lactic-co-glycolic) acid, polylactic acid, polycaprolactone, alginic acid or a salt thereof, polyethylene glycol, a cellulose, a cellulose ether, a carbomer (e.g., Carbopol®), agar-agar, gelatin, glucomannan, galactomannan (e.g., guar gum, locust bean gum, or tara gum), xanthan gum, chitosan, pectin, starch, tragacanth, carrageenan, polyvinylpyrrolidone, polyvinyl alcohol, paraffin, petrolatum, silicates, fibroin, and combinations thereof. The gelling agents described herein are known in the art. Preferably, the gelling agent is hyaluronan.

A pharmaceutical composition may contain, e.g., about 0.5% to about 2% (w/v) (e.g., about 1% to about 2% (w/v)) of hyaluronan relative to solvent. A pharmaceutical composition may contain, e.g., about 5% to about 10% (w/v) (e.g., about 6% to about 8% (w/v)) of methylcellulose relative to solvent. A pharmaceutical composition may contain, e.g., hyaluronan and methylcellulose as a gelling agent (e.g., about 0.5% to about 2% (w/v) of hyaluronan and about 5% to about 10% (w/v) of methylcellulose relative to solvent). A pharmaceutical composition may contain, e.g., a polyoxyethylene-polyoxypropylene block copolymer (e.g., poloxamer) as a gelling agent. A pharmaceutical composition may contain, e.g., about 1% to about 20% (w/v) (e.g., about 1% to about 15% (w/v), about 1% to about 10% (w/v), about 5% to about 20% (w/v), about 5% to about 15% (w/v), about 5% to about 10% (w/v), about 10% to about 20% (w/v), or about 10% to about 15% (w/v)) of a polyoxyethylene-polyoxypropylene block copolymer (e.g., poloxamer) relative to solvent. The poloxamer may be poloxamer 407, poloxamer 188, or a combination thereof. A pharmaceutical composition may contain, e.g., about 0.5% (w/v) to about 20% (w/v) of fibroin as a gelling agent relative to solvent.

Hyaluronan is a hyaluronic acid or a salt thereof (e.g., sodium hyaluronate). Hyaluronans are known in the art and are typically isolated from various bacteria (e.g., *Streptococcus zooepidemicus, Streptococcus equi*, or *Streptococcus pyrogenes*) or other sources, e.g., bovine vitreous humor or rooster combs. The weight-averaged molecular weight (Mw) of hyaluronan is typically about 50 kDa to about 10 MDa. Preferably, Mw of a hyaluronan (e.g., sodium hyaluronate) is about 500 kDa to 6 MDa (e.g., about 500 kDa to about 750 kDa, about 600 kDa to about 1.1 MDa, about 750 kDa to about 1 MDa, about 1 MDa to about 1.25 MDa, about 1.25 to about 1.5 MDa, about 1.5 MDa to about 1.75 MDa, about 1.75 MDa to about 2 MDa, about 2 MDa to about 2.2 MDa, about 2 MDa to about 2.4 MDa). More preferably, the Mw of a hyaluronan (e.g., sodium hyaluronate) is about 620 kDa to about 1.2 MDa or about 1.2 MDa to about 1.9 MDa. Other preferred molecular weight ranges for a hyaluronan include, e.g., about 600 kDa to about 1.2 MDa.

Polyoxyethylene-polyoxypropylene block copolymers are known in the art. A non-limiting example of polyoxyethylene-polyoxypropylene block copolymers is a poloxamer, in which a single polyoxypropylene block is flanked by two polyoxyethylene blocks. Poloxamers are commercially available under various trade names, e.g., Synperonic®, Pluronic®, Kolliphor®, and Lutrol®. A pharmaceutical composition may contain, e.g., a polyoxyethylene-polyoxypropylene block copolymer (e.g., a poloxamer) includes a polyoxypropylene block with a number average molecular weight ($M_n$) of, e.g., about 1,100 g/mol to about 17,400 g/mol (e.g., about 2,090 g/mol to about 2,360 g/mol, about 7,680 g/mol to about 9,510 g/mol, 6,830 g/mol to about 8,830 g/mol, about 9,840 g/mol to about 14,600 g/mol, or about 12,700 g/mol to about 17,400 g/mol). A polyoxyethylene-polyoxypropylene block copolymer (e.g., a poloxamer) may include a polyoxypropylene block with a number average molecular weight ($M_n$) of about 1,100 g/mol to about 4,000 g/mol and a calculated polyoxyethylene content of about 30% to about 85% (w/w). Preferably, a polyoxyethylene-polyoxypropylene block copolymer (e.g., a poloxamer) may include a polyoxypropylene block with a calculated molecular weight of, e.g., about 1,800 g/mol to about 4,000 g/mol. Preferably, the calculated polyoxyethylene content a polyoxyethylene-polyoxypropylene block copolymer (e.g., a poloxamer) may be, e.g., about 70% to about 80% (w/w). Preferably, a polyoxyethylene-polyoxypropylene block copolymer (e.g., a poloxamer) may have a number average molecular weight of, e.g., about 7,680 g/mol to about 14,600 g/mol. Non-limiting examples of poloxamers are poloxamer 407 and poloxamer 188.

Celluloses and cellulose ethers are known in the art. Celluloses and cellulose ethers are commercially available under various tradenames, e.g., Avicel®, Methocel™, Natrosol®, and Tylose®. Non-limiting examples of cellulose ethers include methylcellulose, carboxymethylcellulose, ethylcellulose, hydroxyethylcellulose, methyl hydroxyethylcellulose, hydroxypropyl methylcellulose, or hydroxypropylcellulose. A cellulose ether (e.g., methylcellulose) may have a number average molecular weight ($M_n$) of, e.g., about 5 kDa to about 300 kDa. Methyl-substituted celluloses (e.g., methylcellulose, hydroxypropyl methyl cellulose, or methyl hydroxyethylcellulose) may have methyl content of, e.g., 19% to 35% (e.g., 19% to 30%).

Fibroin is a protein present in silk created by numerous insects. Fibroins are known in the art and are commercially available from various vendors, e.g., Jiangsu SOHO International Group; Simatech, Suzhou, China; Xi'an Lyphar Biotech, Ltd.; Xi'an Rongsheng Biotechnology; Mulberry Farms, Treenway Silks, Sharda Group, Maniar Enterprises, and Wild Fibres. The molecular weight of silk fibroin is typically about 10 kDa to about 500 kDa. Fibroins are described in WO 2017/139684, the disclosure of which is incorporated herein by reference.

Cross-Linked Gelling Agents

Pharmaceutical compositions may contain non-cross-linked or cross-linked gelling agents. Gelling agents may be cross-linked using cross-linking agents known in the art. Preferably, the cross-linked gelling agent is covalently crosslinked. Pharmaceutical compositions (e.g., pharmaceutical dosage forms) including cross-linked gelling agents may be used to control the release profile of an anti-platinum chemoprotectant agent. For example, the release of an anti-platinum chemoprotectant agent from a pharmaceutical composition (e.g., a pharmaceutical dosage form) containing a cross-linked gelling agent may be extended release relative to a reference composition that differs from the pharmaceutical composition only by the lack of cross-linking in the gelling agent in the reference composition. The extension of the release of an anti-platinum chemoprotectant agent may be assessed by comparing $T_{max}$ values for the pharmaceutical composition and the reference composition.

Certain gelling agents, e.g., those having carboxylate moieties (e.g., hyaluronan, alginic acid, and carboxymethylcellulose), can be cross-linked ionically using ionic cross-linking agents (e.g., a multivalent metal ion, e.g., $Mg^{2+}$, $Ca^{2+}$, or $Al^{3+}$). Techniques for ionic cross-linking of gelling agents are known in the art (see, e.g., U.S. Pat. Nos. 6,497,902 and 7,790,699, the disclosures of which are incorporated herein by reference). Typically, gelling agents can be ionically cross-linked in an aqueous solution using multivalent metal ions, e.g., $Mg^{2+}$, $Ca^{2+}$, or $Al^{3+}$, as ionic cross-linking agents. Without wishing to be bound by theory, the metal ions are believed to coordinate to different molecules of the gelling agent (e.g., to pendant carboxylates residing on different molecules of the gelling agent), thereby forming a linkage between these different molecules of the gelling agent.

Certain gelling agents having reactive functional groups, e.g., —OH, —COOH, or —NH$_2$, may be covalently cross-linked. Techniques for covalent cross-linking of gelling agents are known in the art (see, e.g., Khunmanee et al., *J. Tissue Eng.*, 8: 2041731417726464, 2017, the disclosure of which is incorporated herein by reference). Non-limiting examples of covalent cross-linking agents include: 1,4-butanediol diglycidyl ether (BDDE), divinyl sulfone, glutaraldehyde, cyanogen bromide, octeylsuccinic anhydride, acid chlorides, diisocyanates, methacrylic anhydride, boric acid, and sodium periodate/adipic acid dihydrazide.

Other Excipients

Pharmaceutical compositions may contain pharmaceutically excipients other than gelling agents. For example, pharmaceutical compositions may contain, e.g., liquid solvents, tonicity agents, buffering agents, and/or coloring agents. Certain excipients may perform multiple roles. For example, a liquid solvent in addition to its function as a carrier may be used as a tonicity agent and/or buffering agent. Such solvents are known in the art, e.g., salines (e.g., hypertonic saline, hypotonic saline, isotonic saline, or phosphate-buffered saline) and artificial perilymph.

Liquid solvents may be used in pharmaceutical compositions (e.g., pharmaceutical dosage forms) as a vehicle. Liquid solvents are known in the art. Non-limiting examples of liquid solvents include water, salines (e.g., hypertonic saline, hypotonic saline, isotonic saline, or phosphate-buffered saline), artificial perilymph, and tris buffer. Artificial perilymph is an aqueous solution containing NaCl (120-130 mM), KCl (3.5 mM), CaCl$_2$) (1.3-1.5 mM), MgCl$_2$ (1.2 mM), glucose (5.0-11 mM), and buffering agents (e.g., NaHCO$_3$ (25 mM) and NaH$_2$PO$_4$ (0.75 mM), or HEPES (20 mM) and NaOH (adjusted to pH of about 7.5)).

Tonicity agents may be included in pharmaceutical compositions (e.g., pharmaceutical dosage forms) to increase osmolarity relative to that which is afforded by an anti-platinum chemoprotectant agent. Tonicity agents are known in the art. Non-limiting examples of tonicity agents include substantially neutral buffering agents (e.g., phosphate buffered saline, tris buffer, or artificial perilymph), dextrose, mannitol, glycerin, potassium chloride, and sodium chloride (e.g., as a hypertonic, isotonic, or hypotonic saline). Pharmaceutical compositions (e.g., pharmaceutical dosage forms) include sufficient amount of tonicity agents to provide for administration to a subject a hypertonic pharmaceutical dosage form (e.g., a pharmaceutical dosage form having a calculated osmolarity of at least 400 mOsm/L (e.g., at least 500 mOsm/L, at least 600 mOsm/L, or at least 700 mOsm/L), and/or 2,500 mOsm/L or less (e.g., 2,000 mOsm/L, 1,900 mOsm/L or less, 1,800 mOsm/L or less, 1,700 mOsm/L or less, 1,600 mOsm/L or less, or 1,500 mOsm/L or less)). For example, the targeted concentration of a tonicity agent in a pharmaceutical composition (e.g., pharmaceutical dosage form) can be determined, e.g., by (i) subtracting the calculated osmolarity contributions of an anti-platinum chemoprotectant agent and other non-polymeric excipients from the total targeted calculated osmolarity to obtain the targeted calculated osmolarity contribution from the tonicity agent, and (ii) determining the concentration of the tonicity agent by dividing the targeted calculated osmolarity contribution from the tonicity agent by the number of ions and/or molecules produced upon dissolution of the tonicity agent in a liquid solvent. An appropriate amount of the tonicity agent thus can be included in the pharmaceutical composition (e.g., pharmaceutical dosage form).

Buffering agents may be used to adjust the pH of a pharmaceutical composition (e.g., a pharmaceutical dosage form) a substantially neutral pH level. Buffering agents are known in the art. Non-limiting examples of buffering agents include, e.g., phosphate buffers and Good's buffers (e.g., tris, MES, MOPS, TES, HEPES, HEPPS, tricine, and bicine). In addition to the pH control, buffering agents may be used to control osmolarity of the pharmaceutical composition (e.g., pharmaceutical dosage form).

Methods of Preparation

A pharmaceutical composition (e.g., a pharmaceutical dosage form) of the invention may be prepared from an anti-platinum chemoprotectant agent, a gelling agent, and a liquid solvent. A method of preparing a pharmaceutical composition (e.g., a pharmaceutical dosage form) of the invention includes (i) providing the anti-platinum chemoprotectant agent and the gelling agent, and (ii) mixing the anti-platinum chemoprotectant agent and the gelling agent with the liquid solvent to produce the pharmaceutical composition.

The anti-platinum chemoprotectant agent and the gelling agent may be provided, e.g., as a mixture or as separate ingredients. When the anti-platinum chemoprotectant agent and the gelling agent are provided separately, the step (ii) may include, e.g.:

(a) mixing the liquid solvent first with the gelling agent to produce an intermediate mixture and thereafter mixing the intermediate mixture with the anti-platinum chemoprotectant agent;

(b) mixing the liquid solvent first with the anti-platinum chemoprotectant agent to produce an intermediate mixture and thereafter mixing the intermediate mixture with the gelling agent; or (c) mixing a portion of the liquid solvent with the anti-platinum chemoprotectant agent to produce a first mixture, mixing another portion of the liquid solvent with the gelling agent to produce a second mixture, and combining the first and second mixtures.

The following examples are meant to illustrate the invention. They are not meant to limit the invention in any way.

EXAMPLES

Example 1. Preparation of Thiosulfate Salt Formulations

Hyaluronan Gel 1 (0.5M STS, 1% (w/v) hyaluronan)
Sodium thiosulfate pentahydrate (619.75 mg) was dissolved in sterile, distilled water (5 mL) in a sterile vial to produce a clear solution. Hyaluronan (50.30 mg; Pharma Grade 80, Kikkoman Biochemifa company; 0.6-1.2 mDa) was added to the solution, and the resulting mixture was stirred for 8-10 min at 4° C. The resulting solution was filtered through 0.22 μm Millex-GV sterile filter.

Hyaluronan Gel 2 (0.1M STS, 2% (w/v) hyaluronan)
Sodium thiosulfate pentahydrate (124.87 mg) was dissolved in sterile, distilled water (3.031 mL). Methylcellulose (351.01 mg; Methocel® A15 Premium LV, Dow Chemical Company) was dissolved in sterile, distilled water (2.0 mL), and the resulting solution was mixed with the sodium thiosulfate solution. Hyaluronan (100.10 mg; Pharma Grade 80, Kikkoman Biochemifa company; 0.6-1.2 mDa) was added to the resulting mixture and mixed at 4° C. for 10-15 min.

Hyaluronan Gel 3 (0.5M STS, 2% (w/v) hyaluronan)
Sodium thiosulfate pentahydrate (620.35 mg) was dissolved in sterile, distilled water (3 mL). Methylcellulose (350.23 mg; Methocel® A15 Premium LV, Dow Chemical Company) was dissolved in sterile, distilled water (2.0 mL), and the resulting solution was mixed with the sodium thiosulfate solution. Hyaluronan (100.65 mg; Pharma Grade 80, Kikkoman Biochemifa company; 0.6-1.2 mDa) was added to the resulting mixture and mixed at 4° C. for 10-15 min.

Hyaluronan Gel 4 (0.1M STS, 1% (w/v) hyaluronan, manitol)
Hyaluronan (50.09 mg; Pharma Grade 80, Kikkoman Biochemifa company; 0.6-1.2 mDa) was added to water (5 mL). Sodium thiosulfate pentahydrate (124.9 mgs) was added. The pH of the resulting mixture was adjusted to pH7.12 by addition of sodium hydroxide (1N, ca. 0.5 μL). Add appropriate amount of mannitol into the vial to adjust the osmolarity to 1.046 Osm/kg. The viscous solution was filtered through 0.22 μm Millex-GV filter.

Hyaluronan Gel 5 (0.1M STS, 1% (w/v) hyaluronan)
Hyaluronan Gel 5 was prepared according to the procedure described for Hyaluronan Gel 1 with the exception that the amount of sodium thiosulfate pentahydrate was adjusted to provide a 0.1 M concentration of sodium thiosulfate.

Hyaluronan Gel 6 (0.2M STS, 1% (w/v) hyaluronan)
Hyaluronan Gel 6 was prepared according to the procedure described for Hyaluronan Gel 1 with the exception that the amount of sodium thiosulfate pentahydrate was adjusted to provide a 0.2M concentration of sodium thiosulfate.

Hyaluronan Gel 7 (0.3M STS, 1% (w/v) hyaluronan)
Hyaluronan Gel 7 was prepared according to the procedure described for Hyaluronan Gel 1 with the exception that the amount of sodium thiosulfate pentahydrate was adjusted to provide a 0.3M concentration of sodium thiosulfate.

Hyaluronan Gel 8 (0.4M STS, 1% (w/v) hyaluronan)
Hyaluronan Gel 8 was prepared according to the procedure described for Hyaluronan Gel 1 with the exception that the amount of sodium thiosulfate pentahydrate was adjusted to provide a 0.4M concentration of sodium thiosulfate.

Hyaluronan Gel 9 (0.5M STS, 1% (w/v) hyaluronan, Tris (5×))
Hyaluronan (79.99 mg; Pharma Grade 80, Kikkoman Biochemifa company; 0.6-1.2 mDa) was added to Tris buffer (8 mL, AMRESCO-0497-500G). The pH of the resulting mixture was adjusted to pH7.13 by addition of HCl (5N). Sodium thiosulfate pentahydrate (992.60 mg) was added to the above solution. The viscous solution was filtered through 0.22 µm Millex-GV filter.

Hyaluronan Gel 10 (0.5M STS, 1% (w/v) hyaluronan, phosphate buffered saline (5×))
Hyaluronan (70.38 mg; Pharma Grade 80, Kikkoman Biochemifa company; 0.6-1.2 mDa) was added to PBS buffer (7 mL, 5×). Sodium thiosulfate pentahydrate (868.46 mg) was added. The pH of the resulting mixture was adjusted to pH6.99 by addition of NaOH (1N). The viscous solution was filtered through 0.22 Millex-GV filter.

Hyaluronan Gel 11 (0.8M STS, 1% (w/v) hyaluronan)
Hyaluronan Gel 11 was prepared according to the procedure described for Hyaluronan Gel 1 with the exception that the amount of sodium thiosulfate pentahydrate was adjusted to provide a 0.8M concentration of sodium thiosulfate.

Hyaluronan Gel 12 (1 M STS, 0.8% (w/v) hyaluronan)
Hyaluronan Gel 12 was prepared according to the procedure described for Hyaluronan Gel 1 with the exception that the amount of sodium thiosulfate pentahydrate was adjusted to provide a 1M concentration of sodium thiosulfate, and the amount of hyaluronan was adjusted to provide a 0.8% (w/v) concentration of hyaluronan.

Hyaluronan Gel 13 (0.5M STS, 0.82% (w/v) hyaluronan (HYALGAN))
Hyaluronan Gel 13 was prepared by mixing of sodium thiosulfate pentahydrate with hyaluronan (HYALGAN, Fidia Pharma USA, Florham Park, N.J.) to afford the final preparation with 0.82% (w/v) concentration of hyaluronan.

Hyaluronan Gel 14 (0.5M STS, 1% (w/v) hyaluronan (SINGCLEAN))
Hyaluronan Gel 14 was prepared according to the procedure described for Hyaluronan Gel 13 with the exception that hyaluronan (SINGCLEAN, Hangzhouh Singclean Medical Products Co., Ltd., Hangzhou, China) was used in the preparation of this gel.

Hyaluronan Gel 15 (0.5M STS, 1% (w/v) hyaluronan (EUFLEXXA))
Hyaluronan Gel 15 was prepared according to the procedure described for Hyaluronan Gel 13 with the exception that hyaluronan (EUFLEXXA, Ferring Pharmaceuticals Inc., Parsippany, N.J.) was used in the preparation of this gel.

Hyaluronan Gel 16 (0.5M STS, 1% (w/v) hyaluronan (HEALON))
Hyaluronan Gel 16 was prepared according to the procedure described for Hyaluronan Gel 13 with the exception that hyaluronan (HEALON, Johnson & Johnson, New Brunswick, N.J.) was used in the preparation of this gel.

Hyaluronan Gel 17 (1 M STS, 1% (w/v) hyaluronan)
Hyaluronan Gel 17 was prepared according to the procedure described for Hyaluronan Gel 1 with the exception that the amount of sodium thiosulfate pentahydrate was adjusted to provide a 1M concentration of sodium thiosulfate.

Hyaluronan Gel 18 (10% (w/v) N-Acetyl-L-cysteine, 1% (w/v) hyaluronan)
Hyaluronan (39.38 mg; Pharma Grade 80, Kikkoman Biochemifa company; 0.6-1.2 mDa) was added to water (4 mL). N-Acetyl-L-cysteine (399.14 mg) was added. The pH of the resulting mixture was adjusted to pH 7.21 by addition of NaOH (10N, 240 µL). The viscous solution was filtered through 0.22 µM Millex-GV filter. The osmotic pressure was measured as 1.107 Osm/kg.

Other hyaluronan gels may be prepared using the procedures described herein. For example, 1M and 1.5M hyaluronan gels may be prepared according to the same procedure as described for, e.g., Hyaluronan Gel 1 and Hyaluronan Gel 12. Additionally, pH levels of the gels may be adjusted to pH 6.5 to 8.5 using Brønsted acids (e.g., hydrochloric acid) and bases (e.g., sodium hydroxide).

Example 2. Pharmacokinetic Modelling of Perilymph Concentrations

Maximum cochlear platinum levels in humans following high dose cisplatin treatment (100 mg/m$^2$) were modeled through the use of pharmacokinetic (PK) simulations of cisplatin distribution in a human. Kinetic parameters used for simulations were obtained from literature reports on cisplatin population PK (Urien et al, *Br. J. Clin. Pharmacol.*, 57:756-63, 2004) and PK following high dose cisplatin treatment (Andersson et al, *J. Pharm. Sci.*, 85:824-27, 1996). The PK simulations were conducted using WinNonlin (Phoenix 64) PK simulation model 9 (IV infusion, 2 compartment). A plasma-to-cochlea concentration ratio of 1:1 was assumed based on previous results from animal studies, and this assumption is further supported by literature reports showing tissue distribution characteristics of cisplatin (Johnsson et al, *Cancer Chemother. Pharmacol.*, 37:23-31, 1995).

The predicted maximal plasma platinum concentration following cisplatin treatment was determined to be approximately 22 µM. Applying a 30-fold molar stoichiometric ratio results in a concentration of 660 µM (0.66 mM) which, when the molecular weight of thiosulfate is used, results in thiosulfate concentration of 74 µg/mL. Achieving this level of thiosulfate in the human cochlea is expected to provide complete (maximum) protection against cisplatin induced ototoxicity following high dose (e.g., 100 mg/m$^2$) cisplatin treatment.

Example 3. Pharmacokinetic Studies In Vivo

Hyaluronan Gel #1 was administered to male Hartley guinea pigs at a dose of 12% w/v (0.5M, 6.2 mg). The dose volume was fixed (10 µL). Perilymph was sampled at each timepoint (n=5 animals/timepoint) and the concentration of thiosulfate was quantified using a liquid chromatography with tandem mass spectrometry (LC-MS/MS) method.

Hyaluronan Gel 1 achieved maximal perilymph concentration, 868.5 µg/mL (approximately 7.8 mM) at the first time-point sampled (1 h). This maximum perilymph concentration is approximately 10-fold greater than the Hyaluronan Gel 1 concentration predicted to provide 100% protection (minimal efficacious concentration; 74 µg/mL, 0.66 mM) from cisplatin induced ototoxicity. The perilymph $t_{1/2}$ ranged from 2.7 to 6.4 hours. The high perilymph Hyaluronan Gel 1 concentration combined with the relatively long half-life provide a treatment window of 3 h pre to 4 h post cisplatin treatment. In another pharmacokinetic study, healthy human subjects were divided into 4 dose cohorts: Cohort 1, Cohort 2, Cohort 3, and Cohort 4. Each dose cohort contained 8 human subjects randomized to receive either DB-020 or placebo (6/2 randomization; 6 subjects received DB-020, 2 subjects received placebo). Cohort 1 was administered unilaterally, intratympanically 19 mg of sodium thiosulfate as a 0.15M sodium thiosulfate/hyaluronan gel, prepared as described for Hyaluronan Gel 1. Cohort 2 was administered unilaterally, intratympanically 62 mg of sodium thiosulfate as Hyaluronan Gel 1. Cohort 3 was administered unilaterally, intratympanically 124 mg of sodium thiosulfate as Hyaluronan Gel 17. Cohort 4 was administered unilaterally, intratympanically 186 mg of sodium thiosulfate as a 1.5M sodium thiosulfate/hyaluronan gel, prepared as described for Hyaluronan Gel 1. The Placebo subjects were administered 1% w/v aqueous hyaluronan.

Figure 2:
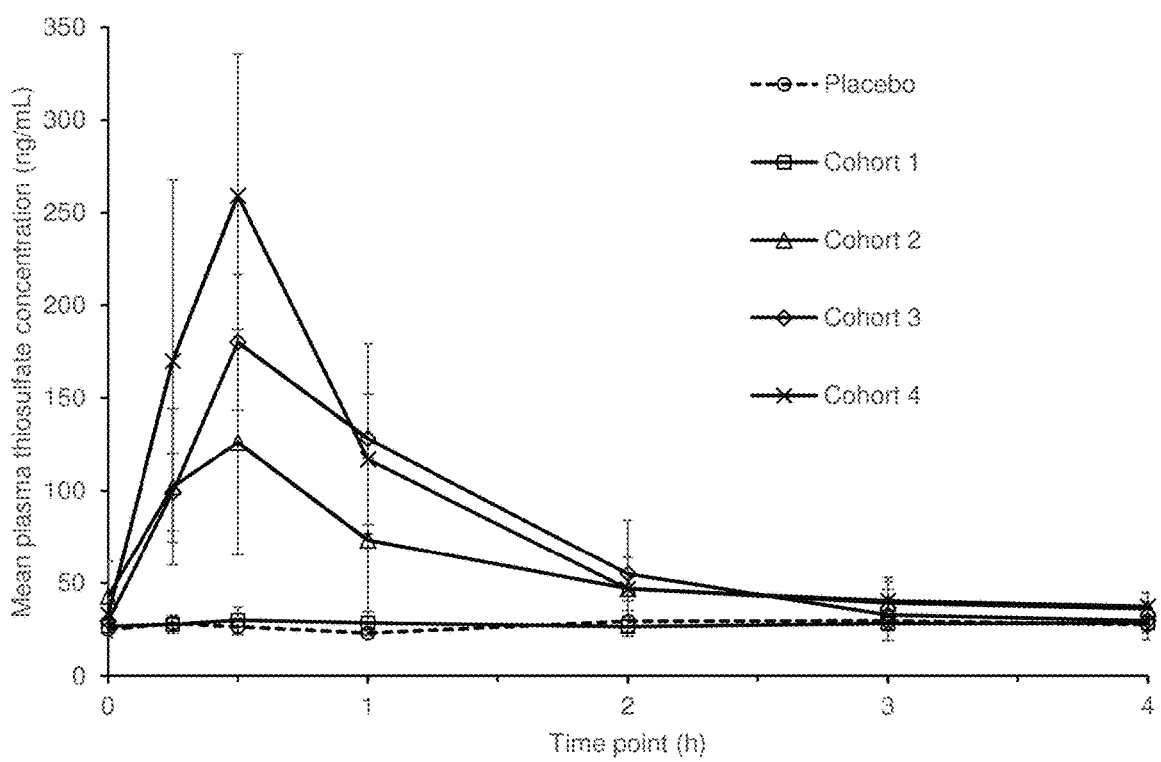
FIG. 2 is a chart showing the profiles (0-4 h) of mean plasma thiosulfate concentrations over time for each tested human cohort. The error bars shown are standard deviations. The X-axis shows time (h), and the Y-axis shows mean plasma thiosulfate concentrations (ng/mL).
Figure 3:
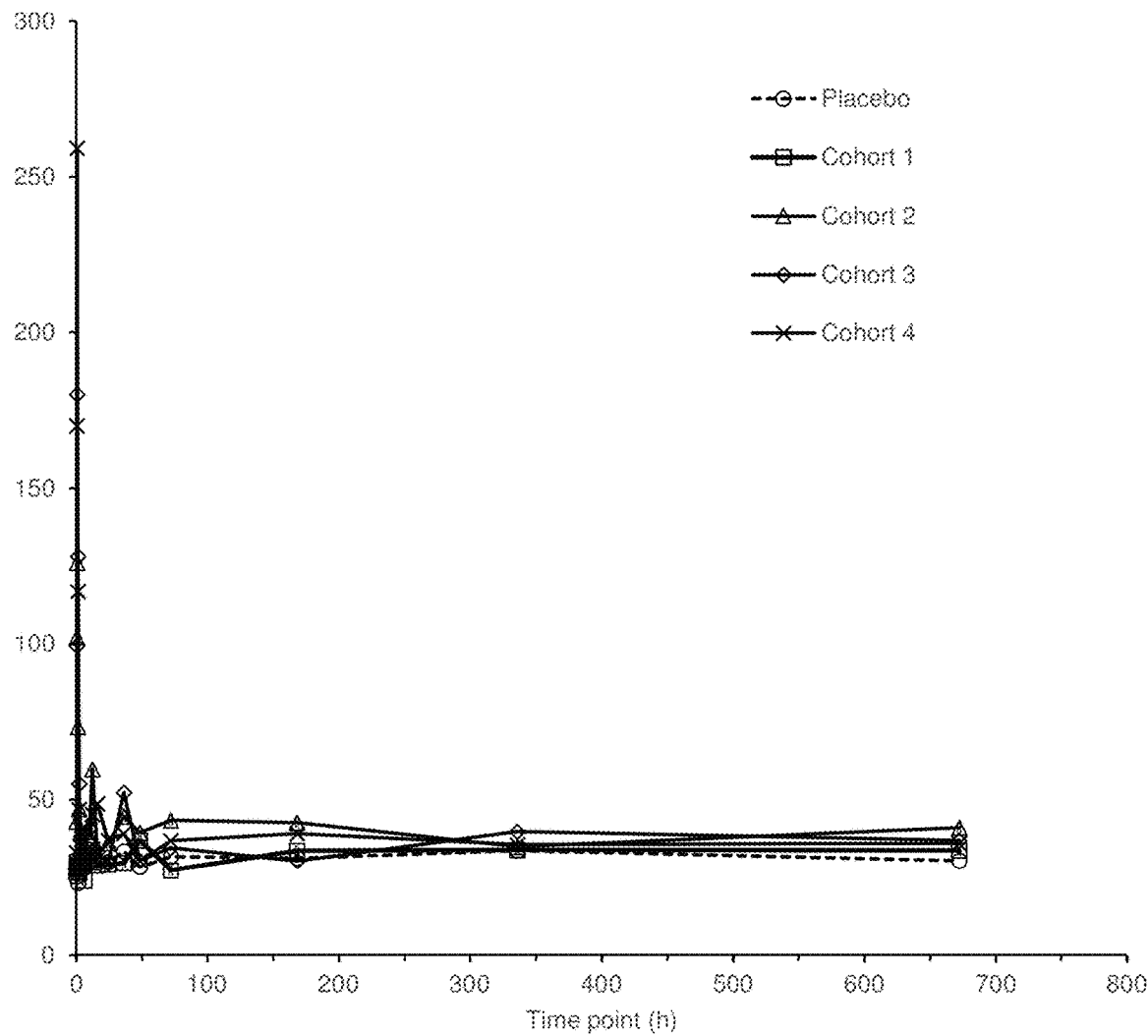
FIG. 3 is a chart showing the profiles (0-672 h) of mean plasma thiosulfate concentrations over time for each tested human cohort. The X-axis shows time (h), and the Y-axis shows mean plasma thiosulfate concentrations (ng/mL).

The results of the studies are shown in Table 1 and 2 and in FIGS. 1-3.

TABLE 1

| Dose | $C_{max, 0-24}$ (ng/mL) | $t_{max}$ (h) | $t_{1/2}$ (h) | $AUC_{0-24}$ (ng*h/mL) |
|---|---|---|---|---|
| Placebo | 37.51 ± 8.59 | 9.06 ± 6.31 | ND | 684.85 ± 105.12 |
| Cohort 1 | 38.42 ± 7.47 | 11.33 ± 2.73 | ND | 685.99 ± 97.86 |
| Cohort 2 | 130.32 ± 60.26 | 0.42 ± 0.13 | 1.11 | 1011.74 ± 257.25 |
| Cohort 3 | 180.00 ± 36.59 | 0.50 ± 0.00 | 0.87 | 860.90 ± 219.42 |
| Cohort 4 | 264.00 ± 68.81 | 0.46 ± 0.10 | 0.63 | 1167.48 ± 204.93 |

TABLE 2

| Cohort | $C_{max}$ Mean ± SD (ng/mL) | Mean ± SD ($\mu$M) [b] | Increase to endogenous [a] | |
|---|---|---|---|---|
| | | | Mean ($\mu$M) | Range ($\mu$M) |
| 2 (12% w/v) | 130.32 ± 60.26 | 1.16 ± 0.54 | 0.83 | 0.04 ± 1.20 |
| 3 (25% w/v) | 180.00 ± 36.59 | 1.61 ± 0.33 | 1.28 | 0.36 ± 1.70 |
| 4 (37% w/v) | 264.00 ± 68.81 | 2.36 ± 0.61 | 2.03 | 0.49 ± 2.65 |

Figure 4:
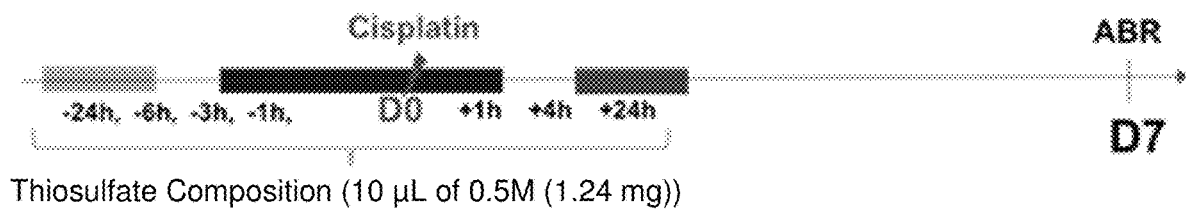
FIG. 4 is a scheme showing the timing of thiosulfate administration relative to cisplatin.
Figure 5A:
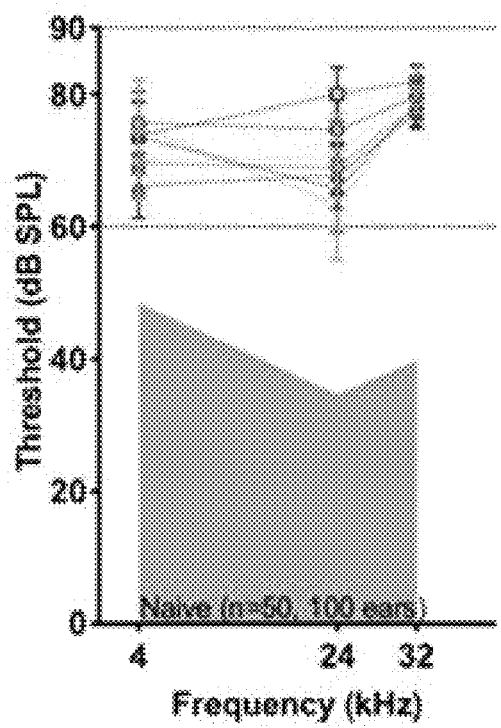
FIG. 5A is a chart showing the average threshold sound pressure levels at 4, 24, and 32 kHz measured during auditory brainstem response (ABR) tests for the control guinea pigs. The baseline thresholds were from historic auditory brainstem response tests on cisplatin-naïve guinea pigs (n=100 ears). The baseline thresholds are shown as a shaded area curve. The X-axis shows sound frequency in kHz, and the Y-axis shows the response threshold in decibel of sound pressure level (dB SPL).
Figure 5B:
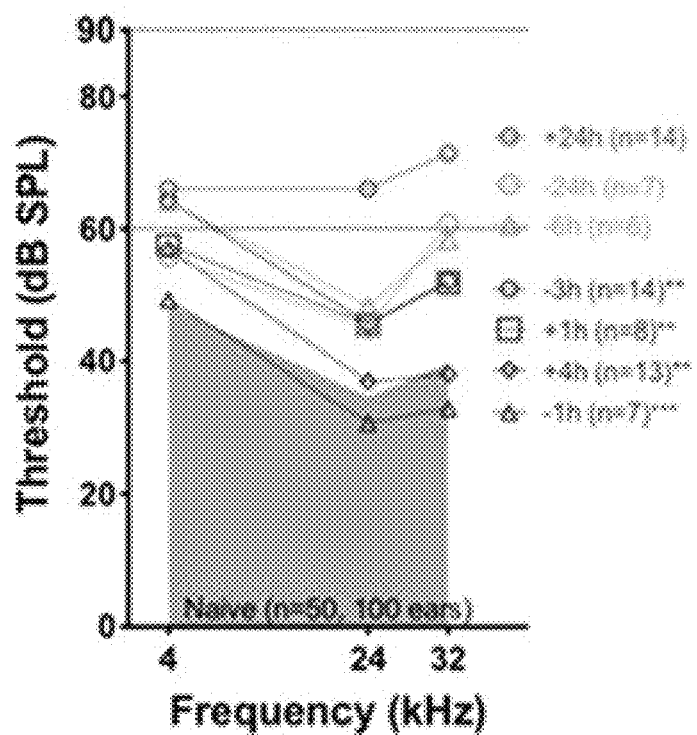
FIG. 5B is a chart showing the average threshold sound pressure levels at 4, 24, and 32 kHz measured during auditory brainstem response (ABR) tests for the guinea pigs administered sodium thiosulfate to one ear each followed by a cisplatin challenge. The baseline thresholds were from historic auditory brainstem response tests on cisplatin-naïve guinea pigs (n=100 ears). The baseline thresholds are shown as a shaded area curve. The X-axis shows sound frequency in kHz, and the Y-axis shows the response threshold in decibel of sound pressure level (dB SPL). The data shown are Mean±standard error of the mean (SEM); two way analysis of variance (ANOVA);  $P<0.01$; *$P<0.001$ Treated ears vs. Untreated ears (compare to FIG. 5A).
Figure 6:
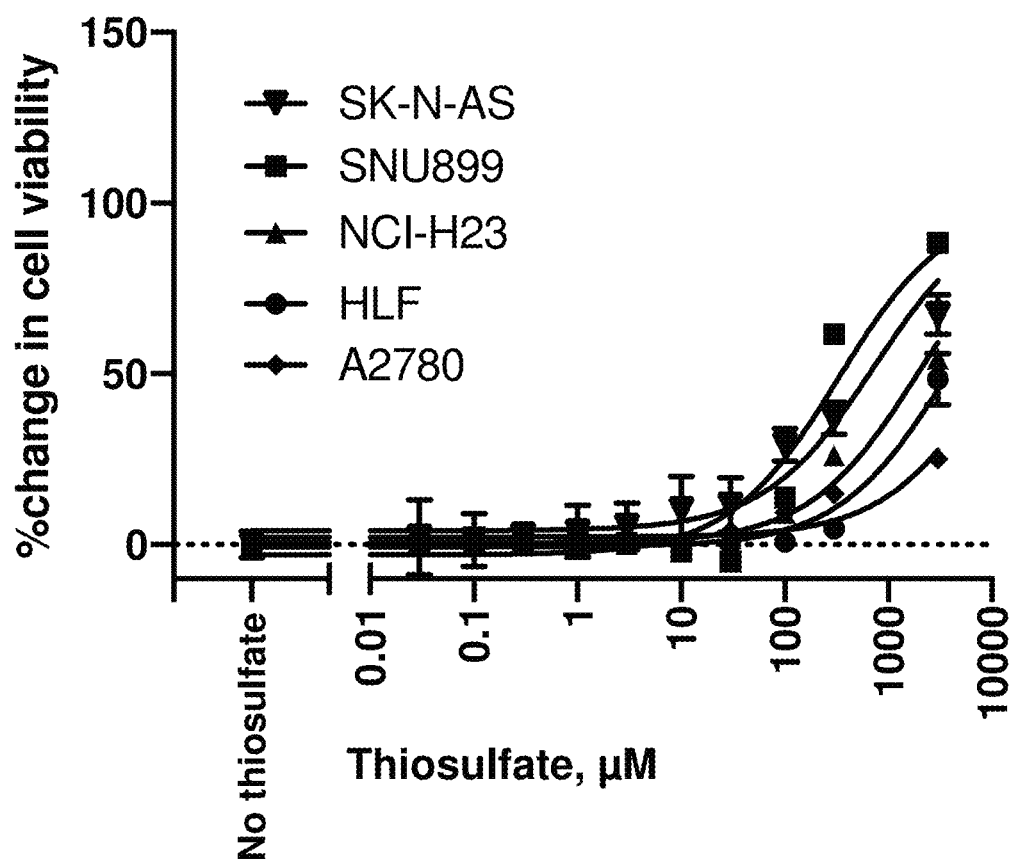
FIG. 6 is a chart showing the concentration dependence for thiosulfate (DB-020) in humor tumor cell lines treated with cisplatin at 15 µM. The following tumor cell lines were used; SH-N-AS (brain, neuroblastoma), SNU899 (larynx, squamous cell carcinoma), NCI-H23 (lung, non-small cell), HLF (Liver, undifferentiated hepatocellular carcinoma) and A2780 (Ovary, carcinoma).
Figure 7:
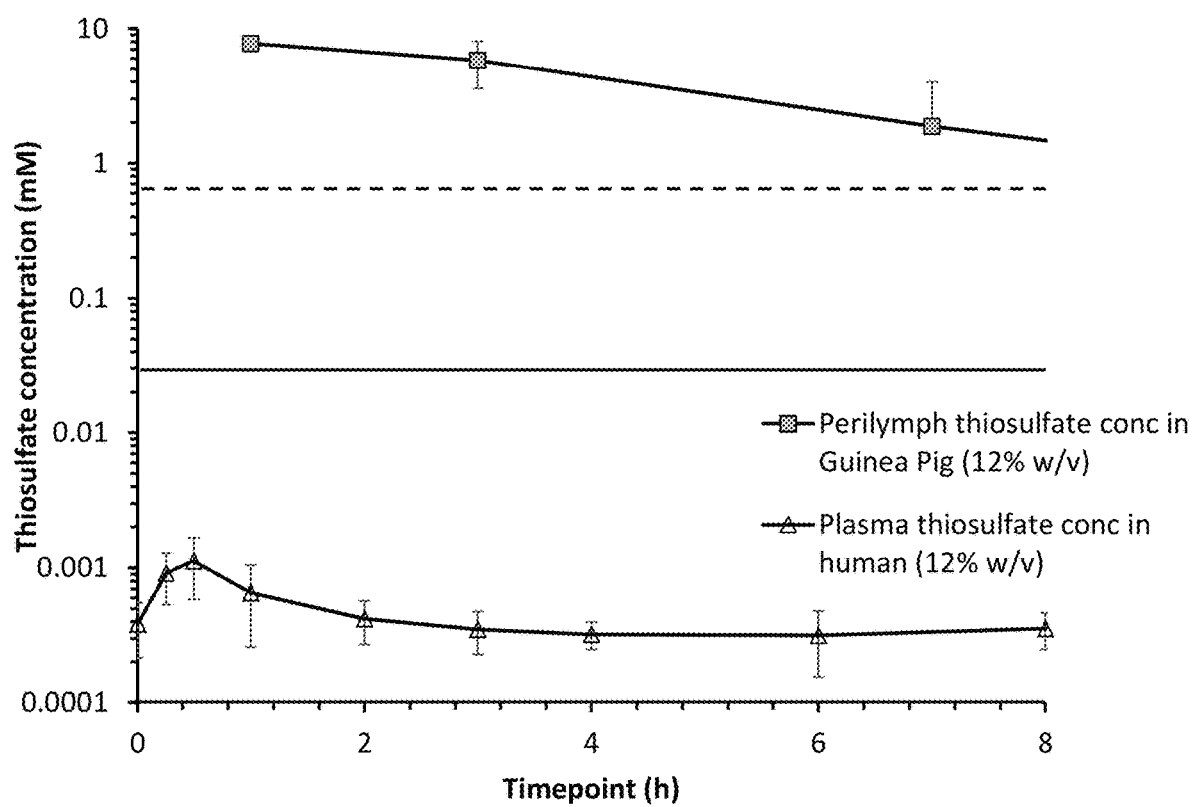
FIG. 7 is a chart showing the profiles (0-8 h) of mean thiosulfate concentrations (mM) over time in plasma (human) and perilymph (guinea pig) following administration of Hyaluronan Gel 1 (12% w/v, 0.5M sodium thiosulfate). The horizontal solid line shows the 30 µM level below which plasma thiosulfate levels should be. The horizontal dotted line shows the 660 µM (0.66 mM) level above which perilymph thiosulfate levels should be.

[a] increase to endogenous = (mean thiosulfate $C_{max}$) − (mean thiosulfate Placebo levels)
[b] MW thiosulfate = 112 g/mol Example 4. Pharmacodynamic Studies In Vivo To assess the treatment window for a sodium thiosulfate gel in relation to cisplatin administration, a single dose of 1.24 mg Hyaluronan Gel 1 was administered intratympanically (IT) to the left ear of guinea pigs either 24 hours, 6 hours, 3 hours, or 1 hour prior to, or 1 hour, 4 hours or 24 hours following cisplatin (single 10 mg/kg IV bolus; FIG. 4). All right control ears that were not treated with Hyaluronan Gel 1 demonstrated significant threshold shifts (i.e., hearing loss) compared to naïve animals (FIG. 5A). Hyaluronan Gel 1 dosed from 3 hours prior to 4 hours post cisplatin administration, provided protection from cisplatin-induced hearing loss relative to control ears untreated by Hyaluronan Gel 1 (FIG. 5B). Hyaluronan Gel 1 was moderately less effective at protecting from cisplatin-induced hearing loss when administered more distally to cisplatin treatment (e.g., >6 h prior or 24 h post cisplatin dose). Maximum protection was observed when Hyaluronan Gel 1 was dosed 1 h prior to cisplatin administration indicating the highest level of protection can be achieved when Hyaluronan Gel 1 is administered prior to and, preferably, proximally to cisplatin treatment Other Embodiments Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method of mitigating platinum-induced hearing loss in a subject in need thereof, the method comprising (i) administering to the subject by intratympanically or transtympanically injecting an effective amount of a hypertonic composition comprising 0.5M-1.0M of a thiosulfate salt, and (ii) administering a platinum-based antineoplastic agent 1 to 3 hours following step (i).

2. The method of claim 1, wherein the thiosulfate salt is an alkaline thiosulfate salt, ammonium thiosulfate salt, or a solvate thereof.

3. The method of claim 1, wherein 200-1,000 $\mu$L of the hypertonic pharmaceutical composition are administered to the round window of the subject.

4. The method of claim 1, wherein the effective amount is an amount that produces a plasma thiosulfate concentration that is 30 $\mu$M or less at the time the platinum-based antineoplastic agent is administered.

5. The method of claim 1, wherein the effective amount is an amount that produces a maximum thiosulfate concentration of 0.6-10 mmol/L by 1 h post administration.

6. The method of claim 1, wherein the effective amount is an amount that produces a thiosulfate concentration of 0.1-2 mmol/L by 7 h post administration in the subject's cochlea.

7. The method of claim 1, wherein the hypertonic composition produces a cochlear thiosulfate $C_{max}$ that is at least 30 times greater than a cochlear $C_{max}$ of the platinum-based antineoplastic agent, wherein the cochlear $C_{max}$ concentrations are modeled by a pharmacokinetic simulation of intravenous infusion in a two compartment model.

\* \* \* \* \*